US011350877B2

(12) United States Patent
Zhang et al.

(10) Patent No.: US 11,350,877 B2
(45) Date of Patent: Jun. 7, 2022

(54) SMART SHOES WITH ADAPTIVE SAMPLING FOR REHABILITATION AND HEALTH MONITORING

(71) Applicants: Wenlong Zhang, Chandler, AZ (US); Julie Vuong, Phoenix, AZ (US); Zhi Qiao, Tempe, AZ (US); Prudhvi Chinimilli, Tempe, AZ (US)

(72) Inventors: Wenlong Zhang, Chandler, AZ (US); Julie Vuong, Phoenix, AZ (US); Zhi Qiao, Tempe, AZ (US); Prudhvi Chinimilli, Tempe, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 339 days.

(21) Appl. No.: 16/580,791

(22) Filed: Sep. 24, 2019

(65) Prior Publication Data

US 2020/0093438 A1    Mar. 26, 2020

Related U.S. Application Data

(60) Provisional application No. 62/735,653, filed on Sep. 24, 2018.

(51) Int. Cl.
*A61B 5/00* (2006.01)
*A61B 5/103* (2006.01)
(Continued)

(52) U.S. Cl.
CPC .............. *A61B 5/6807* (2013.01); *A43B 3/34* (2022.01); *A61B 5/0004* (2013.01);
(Continued)

(58) Field of Classification Search
CPC ... A61B 5/6807; A61B 5/1038; A61B 5/1112; A61B 5/1118; A61B 5/6843;
(Continued)

(56) References Cited

U.S. PATENT DOCUMENTS

| 5,813,142 A * | 9/1998 | Demon | A43B 3/0005 |
| | | | 36/28 |
| 5,875,571 A * | 3/1999 | Huang | A43B 3/0005 |
| | | | 36/132 |

(Continued)

OTHER PUBLICATIONS

Lee, I-Min, Shiroma, Eric J., Lobelo, Felipe, Puska, Pekka, Blair, Steven N., and Katzmarzyk, Peter T. "Effect of Physical Inactivity on Major Non-Communicable Diseases Worldwide: an Analysis of Burden of Disease and Life Expectancy." The Lancet vol. 380 No. 9838 (2012): pp. 219-229. DOI 10.1016/S0140-6736(12)61031-9. https://www.ncbi.nlm.nih.gov/pubmed/22818936.
(Continued)

*Primary Examiner* — May A Abouelela
(74) *Attorney, Agent, or Firm* — Snell & Wilmer L.L.P.

(57) ABSTRACT

A smart shoe, smart shoe system, and a method of a smart shoe are disclosed. A smart shoe system may be used for monitoring patient activity. The smart shoe system may include a shoe having a plurality of pneumatic pressure sensors. The pressure sensors may be configured to detect pressure at a plurality of points in the sole of the shoe. The smart shoe may also include a microprocessor coupled to the pressure sensors and a GPS integrated circuit. The GPS integrated circuit may be used for correlating position of the smart shoe system to activity data generated by the plurality of pressure sensors. Additionally, the smart shoe system may include a flash memory storage for storing data generated by the microprocessor and pressure sensors.

13 Claims, 6 Drawing Sheets

(51) Int. Cl.
  *A61B 5/11* (2006.01)
  *A43B 3/34* (2022.01)
(52) U.S. Cl.
  CPC .......... *A61B 5/0022* (2013.01); *A61B 5/1038* (2013.01); *A61B 5/1112* (2013.01); *A61B 5/1118* (2013.01); *A61B 5/6843* (2013.01); *A61B 5/7267* (2013.01); *A61B 2560/0214* (2013.01); *A61B 2560/0475* (2013.01); *A61B 2562/0247* (2013.01); *A61B 2562/046* (2013.01)
(58) Field of Classification Search
  CPC ... A61B 5/0004; A61B 5/0022; A61B 5/7267; A61B 2562/046; A61B 2560/0214; A61B 2560/0475; A61B 2562/0247; A61B 5/112; A61B 5/1123; A43B 3/0005; G01G 19/44
  USPC ................................................ 600/587, 592
  See application file for complete search history.

(56) References Cited

U.S. PATENT DOCUMENTS

| | | | | |
|---|---|---|---|---|
| 7,107,706 | B1* | 9/2006 | Bailey, Sr. ........... | A43B 3/0005 36/29 |
| 7,204,041 | B1* | 4/2007 | Bailey, Sr. ........... | A43B 3/0005 36/1 |
| 7,219,449 | B1* | 5/2007 | Hoffberg ............ | A43B 1/0054 36/29 |
| 7,771,371 | B2* | 8/2010 | Avni ....................... | G01L 5/008 600/592 |
| 7,911,339 | B2* | 3/2011 | Vock ....................... | A43D 1/00 340/540 |
| 8,384,551 | B2* | 2/2013 | Ross ........................ | A43B 7/00 340/573.7 |
| 10,524,531 | B2* | 1/2020 | Roberts ................. | A43B 3/0005 |
| 10,736,542 | B2* | 8/2020 | Krimmer ............. | A43B 17/006 |
| 11,064,758 | B2* | 7/2021 | Dervish ................ | A43B 7/142 |
| 2003/0163287 | A1* | 8/2003 | Vock ....................... | G01P 3/50 702/187 |
| 2008/0167580 | A1* | 7/2008 | Avni ....................... | A43D 1/00 600/587 |
| 2009/0326341 | A1* | 12/2009 | Furlan .................. | A61B 5/1036 600/301 |
| 2011/0005103 | A1* | 1/2011 | Krouse ................ | A43B 3/0005 36/134 |
| 2011/0131839 | A1* | 6/2011 | Ballin .................. | A43B 13/186 36/141 |
| 2011/0214501 | A1* | 9/2011 | Ross ..................... | A43B 3/0005 73/172 |
| 2011/0301504 | A1* | 12/2011 | Lan ....................... | A61B 5/1036 600/592 |
| 2013/0150755 | A1* | 6/2013 | Kubiak .................. | A61B 5/11 600/592 |
| 2015/0133754 | A1* | 5/2015 | Freeman ................ | G16Z 99/00 600/323 |
| 2015/0177081 | A1* | 6/2015 | Steier .................. | A61B 5/1038 600/592 |
| 2016/0349076 | A1* | 12/2016 | Campos Gallo .......... | G01L 1/16 |
| 2017/0213382 | A1* | 7/2017 | Torvinen ................ | A61B 5/112 |
| 2018/0160975 | A1* | 6/2018 | London .................. | A61B 5/1118 |
| 2018/0325207 | A1* | 11/2018 | Krasnow ................ | A43B 3/0015 |
| 2018/0338561 | A1* | 11/2018 | Destrian ................ | A63F 13/212 |
| 2019/0000186 | A1* | 1/2019 | Mou ........................ | F04B 45/047 |
| 2019/0150565 | A1* | 5/2019 | Li ........................... | A43B 3/0005 |
| 2019/0373984 | A1* | 12/2019 | Wijesundara .......... | A43B 7/1475 |
| 2020/0102043 | A1 | 4/2020 | Zhang et al. | |
| 2020/0121201 | A1* | 4/2020 | Redtel ................... | A61B 5/02125 |
| 2020/0178849 | A1* | 6/2020 | Cheng ................... | A61B 5/1126 |
| 2020/0297073 | A1* | 9/2020 | Li ........................... | A43B 13/206 |
| 2021/0145622 | A1* | 5/2021 | Riffel ....................... | A43B 3/00 |

OTHER PUBLICATIONS

"Physical Activity," last modified Feb. 23, 2018, accessed Sep. 13, 2018, http://www.who.int/news-room/fact-sheets/detail/physical-activity.

Chodzko-Zajko, Wojtek J., Proctor, David N., Fiatarone Singh, Maria A., Minson, Christopher T., Nigg, Claudio R., Salem, George J., and Skinner, James S. "Exercise and Physical Activity for Older Adults." Medicine & Science in Sports & Exercise vol. 41 No.7 (2009): pp. 1510-1530. DOI 10.1249/MSS.0b013e3181a0c95c. https://journals.lww.com/acsm-msse/fulltext/2009/07000/Exercise_and_Physical_Activity_for_Older_Adults.20.aspx.

"Physical Inactivity: A Global Public Health Problem," accessed Aug. 23, 2018, http://www.who.int/dietphysicalactivity/factsheet_inactivity/en/.

Warburton, Darren E.R., Nicol, Crystal Whitney, and Bredin, Shannon S.D. "Health Benefits of Physical Activity: the Evidence." Canadian Medical Association Journal vol. 174, No. 6 (2006): pp. 801-809. DOI 10.1503/cmaj.051351. https://www.ncbi.nlm.nih.gov/pmc/articles/PMC1402378/.

Kong, Kyoungchul, and Tomizuka, Masayoshi. "A Gait Monitoring System Based on Air Pressure Sensors Embedded in a Shoe." IEEE/ASME Transactions on Mechatronics vol. 14 No. 3 (2009): pp. 358-370. DOI 10.1109/TMECH.2008.2008803. https://ieeexplore.ieee.org/document/4813239/.

Headon, Robert, and Curwen, Rupert. "Recognizing Movements from the Ground Reaction Force." Proceedings of the 2001 Workshop on Perceptive User Interfaces, pp. 1-8. Orlando, FL, Nov. 15-16, 2001. DOI 10.1145/971478.971523. https://dl.acm.org/citation.cfm?doid=971478.971523.

Schepers, H. Martin, Koopman, H.F.J.M., and Veltink, Peter H. "Ambulatory Assessment of Ankle and Foot Dynamics." IEEE Transactions on Biomedical Engineering, vol. 54 No. 5 (2007): pp. 895-902. DOI 10.1109/TBME.2006.889769. https://ieeexplore.ieee.org/document/4155014/.

Deng, Wenhao, Papavasileiou, Ioannis, Qiao, Zhi, Zhang, Wenlong, Lam, Kam-Yiu., and Han, Song. "Advances in Automation Technologies for Lower Extremity Neurorehabilitation: A Review and Future Challenges." IEEE Reviews in Biomedical Engineering, vol. 11 (2018): pp. 289-305. DOI 10.1109/RBME.2018.2830805. https://ieeexplore.ieee.org/document/8354783/.

Rueterbories, Jan, Spaich, Erika G., Larsen, Birgit, and Andersen, Ole K. "Methods for Gait Event Detection and Analysis in Ambulatory Systems." Medical Engineering & Physics vol. 32 No. 6 (2010): pp. 545-552. DOI 10.1016/j.medengphy.2010.03.007. https://www.sciencedirect.com/science/article/pii/S1350453310000718.

Wachtel, SeanWolfgang, Hassett, Breanna, Qiao, Zhi, Chinimilli, Prudhvi Tej, and Zhang, Wenlong. "Design and Characterization of Shoe Embedded Pressure Sensors for Gait Analysis and Rehabilitation." Proceedings of the 2017 Design of Medical Devices Conference. DMD2017-3424: pp. V001T05A005. Minneapolis, MN, Apr. 10-13, 2017. DOI 10.1115/DMD2017-3424. https://proceedings.asmedigitalcollection.asme.org/proceed ing.aspx?articleID=2661337.

Rezaie, Hamed, and Ghassemian, Mona. "An Adaptive Algorithm to Improve Energy Efficiency in Wearable Activity Recognition Systems." IEEE Sensors Journal, vol. 17 No. 16 (2017): pp. 5315-5323. DOI 10.1109/JSEN.2017.2720725. https://ieeexplore.ieee.org/abstract/document/7959571/.

Klotz, Irene "GPS Inhalers Track Asthma Triggers," ABC Science Online, last modified Apr. 13, 2009, accessed Feb. 8, 2019, http://www.abc.net.au/science/articles/2009/04/13/2540052.htm.

Seto, Edmund Y.W., Knapp, Freyja, Zhong, Bo, and Yang, Changhong. "The Use of a Vest Equipped with a Global Positioning System to Assess Water-Contact Patterns Associated with Schistosomiasis." Geospatial Health vol. 1 No. 2 (2007): pp. 233-241. DOI 10.4081/gh.2007.271. https://www.geospatialhealth.net/index.php/gh/article/view/271.

Marshall, Simon J., Levy, Susan S., Tudor-Locke, Catrine E., Kolkhorst, Fred W., Wooten, Karen M., Ji, Ming, Macera, Caroline A., and Ainsworth, Barbara E. "Translating Physical Activity Recommendations into a Pedometer-Based Step Goal: 3000 Steps in 30

(56) References Cited

OTHER PUBLICATIONS

Minutes." American Journal of Preventive Medicine vol. 36 No. 5 (2009): pp. 410-415. DOI 10.1016/j.amepre.2009.01.021. https://www.sciencedirect.com/science/article/pii/S0749379709000877.

Papavasileiou, Ioannis, Wenlong Zhang, and Han, Song. "Real-Time Data-Driven Gait Phase Detection Using Ground Contact Force Measurements: Algorithms, Platform Design and Performance." Smart Health vol. 1-2 (2017): pp. 34-49. DOI 10.1016/j.smhl.2017.03.001. https://ieeexplore.ieee.org/document/7545845/.

* cited by examiner

SMART SHOES WITH ADAPTIVE SAMPLING FOR REHABILITATION AND HEALTH MONITORING

CROSS-REFERENCE TO RELATED APPLICATION

This application claims priority to, and the benefit of, U.S. Provisional Application Ser. No. 62/735,653 filed on Sep. 24, 2018, and entitled "SMART SHOES WITH ADAPTIVE SAMPLING FOR REHABILITATION AND HEALTH MONITORING." The above application is hereby incorporated by reference in its entirety.

TECHNICAL FIELD

The present disclosure relates to healthcare, and in particular to patient health monitoring devices and approaches for use.

BACKGROUND

Prior patient monitoring systems, for example systems intended to monitor activity levels of outpatients, have suffered from various deficiencies. Accordingly, improved patient monitoring systems and improved patient monitoring methods remain desirable.

SUMMARY

An example embodiment is a smart shoe system for monitoring patient activity. The smart shoe system may include a shoe having a plurality of pneumatic pressure sensors. The pressure sensors may be configured to detect pressure at a plurality of points in the sole of the shoe. The smart shoe system may include a microprocessor coupled to the pressure sensors and a GPS integrated circuit. The GPS integrated circuit may be for correlating position of the smart shoe system to activity data generated by the plurality of pressure sensors. The smart shoe system may include a flash memory storage for storing data generated by the microprocessor and pressure sensors.

Another example embodiment is a method for monitoring an activity level of a patient. The method may include wearing, by the patient, a smart shoe system, recording, by the smart shoe system, activity information for the patient, and transmitting, to a medical provider and over an electronic network, the activity information. The smart shoe system may include a shoe having a plurality of pneumatic pressure sensors. The pressure sensors may be configured to detect pressure at a plurality of points in the sole of the shoe. The smart shoe system may include a microprocessor coupled to the pressure sensors and a GPS integrated circuit. The GPS integrated circuit may be for correlating position of the smart shoe system to activity data generated by the plurality of pressure sensors. The smart shoe system may include a flash memory storage for storing data generated by the microprocessor and pressure sensors.

Yet another example embodiment is a smart shoe. The smart shoe may include a plurality of pneumatic pressure sensors. The pressure sensors may be configured to detect pressure at a plurality of points in the sole of the shoe. The smart shoe may include a microprocessor coupled to the pressure sensors and a GPS integrated circuit. The GPS integrated circuit may be used for correlating position of the smart shoe system to activity data generated by the plurality of pressure sensors. The smart shoe may include a flash memory storage for storing data generated by the microprocessor and pressure sensors.

BRIEF DESCRIPTION OF THE DRAWINGS

With reference to the following description and accompanying drawings.

DETAILED DESCRIPTION

Figure 1:
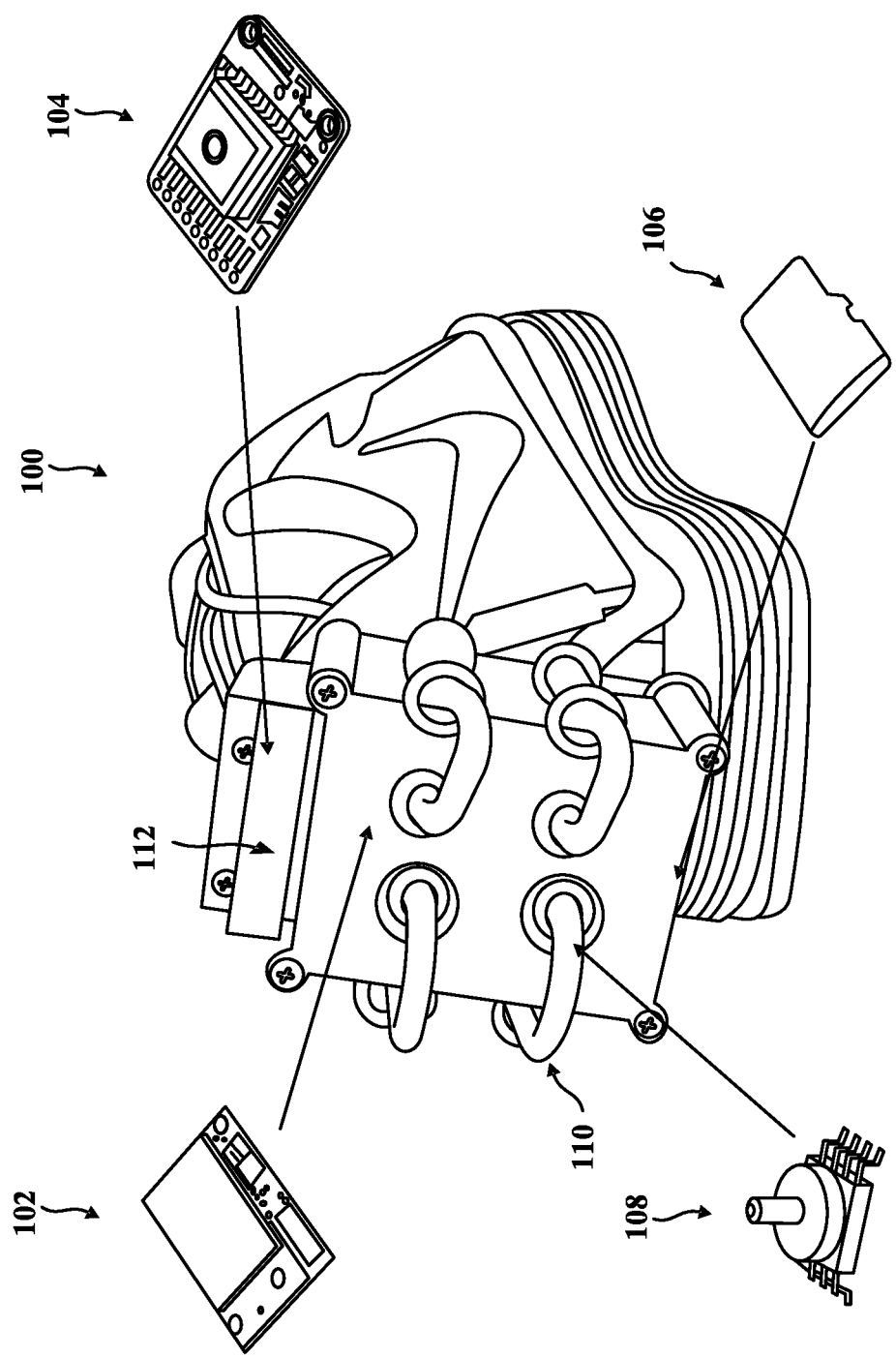
FIG. 1 illustrates use of an exemplary smart shoe system in accordance with an exemplary embodiment.

The following description is of various exemplary embodiments only, and is not intended to limit the scope, applicability or configuration of the present disclosure in any way. Rather, the following description is intended to provide a convenient illustration for implementing various embodiments including the best mode. As will become apparent, various changes may be made in the function and arrangement of the elements described in these embodiments without departing from principles of the present disclosure.

For the sake of brevity, conventional techniques for remote patient monitoring, compliance assessment, the like or some combination of these may not be described in detail herein. Furthermore, the connecting lines shown in various figures contained herein are intended to represent exemplary functional relationships, exemplary physical couplings between various elements, or both exemplary functional relationships and exemplary physical couplings between various elements. It should be noted that many alternative or additional functional relationships or physical connections may be present in a smart shoe system, components thereof, or both.

Principles of the present disclosure contemplate the use of smart shoe systems, for example for use in monitoring patient activity. In an exemplary embodiment, an adaptive sampling algorithm may be utilized in a pair of smart shoes for patients to use as a daily health monitoring device. The main hardware of each smart shoe, which may come in pairs, features four pneumatic pressure sensors that measure ground contact forces (GCFs), and may also include a global positioning system (GPS) to track the location of the user. Sampling rate of the pressure sensors and the GPS may be changed based on the activity, e.g., either walking or sitting, detected from the user's GCFs. In various operational testing, the adaptive algorithm achieved a 95% reduction in data size compared to sampling with the highest settings from all system components. Collected GPS information from a subject's activities may be utilized, displayed, or both utilized and displayed, for example collected GPS information may be displayed on a map, to provide context for patient monitoring information.

Based on the 57 million deaths worldwide recorded in 2008, it is estimated that over 5.3 million deaths could be avoided per year if all those who are inactive get enough physical activity. Physical inactivity is linked with non-communicable diseases (NCDs) such as cardiovascular disease, cancer, and diabetes and with the progression of age-related mobility limitations in older adults. Reasons for physical inactivity may be due to sedentary lifestyles influenced by modernization and environmental factors such as areas with violence, lack of recreational facilities or parks, pollution, or dense traffic. Although physical inactivity may contribute to such conditions, specifically for diabetes and cardiovascular disease, physical activity is associated with reduced risk of premature death once these diseases have been established. Depending on the patient, some rehabilitation or intervention programs may advise incorporating physical activity with specific instructions on a regular basis to help improve or maintain health conditions. Between follow-up visits with professionals, monitoring activities with specialized devices during outpatient time periods may be beneficial to better evaluate the progress of treatment, assess patient conditions, and provide useful feedback for both patients and their caregivers.

As disclosed herein, exemplary principles, algorithms, and systems improve the functioning of various associated computing devices. For example, use of certain adaptive algorithms results in improved data efficiency and extended battery life for an electronic system integrated into a smart shoe. In one exemplary embodiment, use of a certain adaptive algorithm reduced the collected data size for 95% while still effectively capturing the human walking dynamics. Thus, associated storage devices, such as flash storage, may be made smaller, cheaper, or both smaller and cheaper; similarly, associated network communications components, such as wireless transceivers, may be made simpler, lower power, or both simpler and lower power due to the need to communicate smaller amounts of data.

Figure 2:
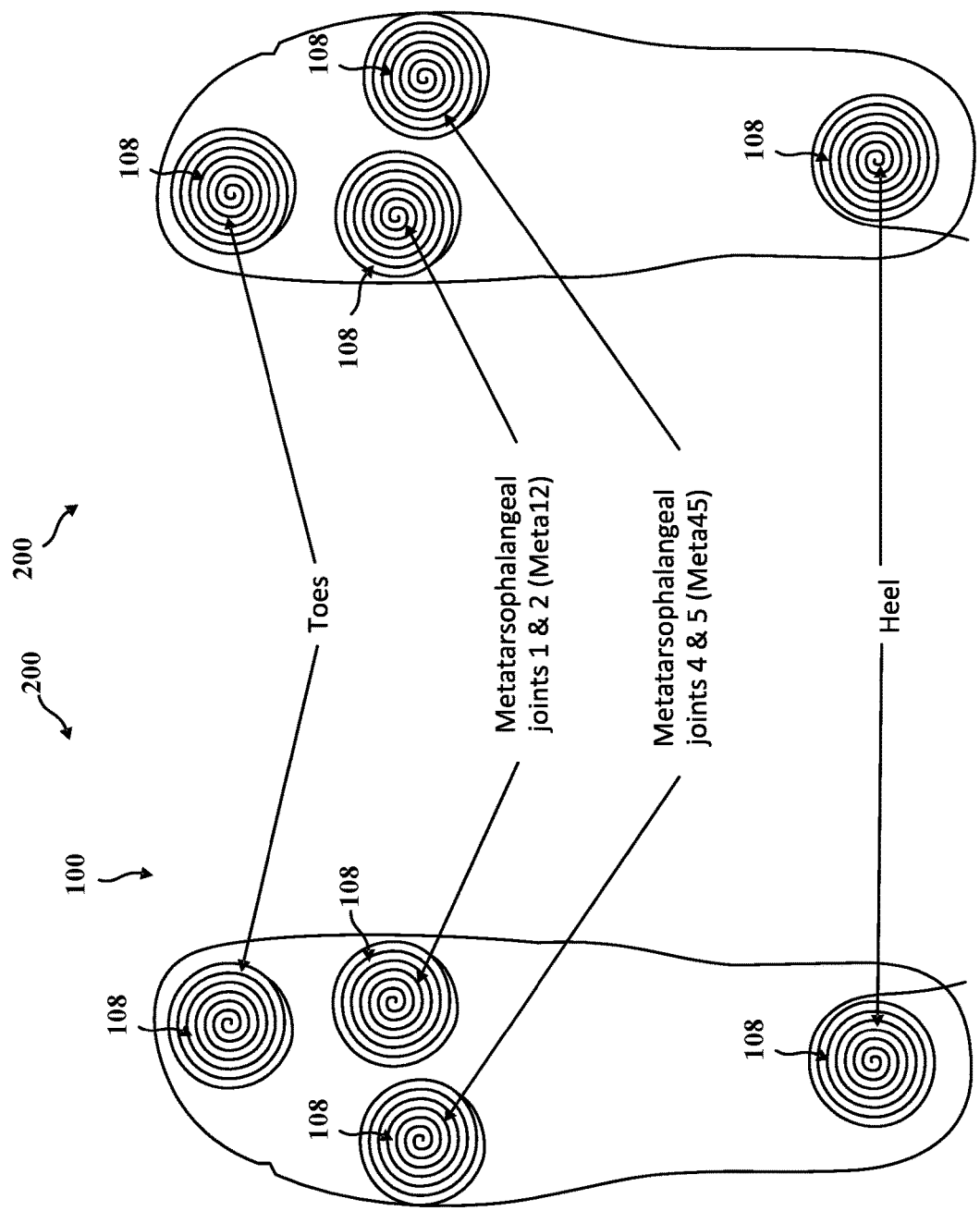
FIG. 2 illustrates the bottom surface of a pair of shoe soles of a smart shoe system, with labeled sensing points at each of the silicone tube coils, in accordance with an exemplary embodiment.

With reference now to FIG. 1 and FIG. 2, an exemplary smart shoe system 100 comprises various computing components, network components, or both computing components and networking components, such as a microprocessor 102; a GPS chip, GPS module, or GPS integrated circuit (e.g., the GPS module 104); memory 106, e.g., flash memory storage (e.g., MicroSD Card), or the like, or some combination of these. Additionally, system 100 may comprise various pressure sensors 108, tubes 110, and so forth. In one exemplary embodiment, system 100 utilizes 4 pressure sensors 108 per shoe sole 200, with the sensors 108 placed generally at the heel, the toe, and the metatarsophalangeal joints, as illustrated in FIG. 2. However, pressure sensors 108 may be placed in any appropriate location to detect pressure data for use by system 100.

FIG. 1 illustrates use of an exemplary smart shoe system 100 in accordance with an exemplary embodiment. More specifically, FIG. 1 illustrates a right smart shoe and the major internal components inside the smart shoe's sensor box 112.

In a specific example, a GPS module 104 has been implemented into the design to obtain the user's location for contextual data. The sensor box 112 may be designed to accommodate for the addition of a Universal Asynchronous Receiver-Transmitter (UART) board to communicate with the GPS module 104, a console board to communicate with the microprocessor 102 via USB, and a microSD card board to store data externally. Exemplary weight and dimensions of an example sensor box are 97.3 g and 75.8×58.7×53.3 mm, respectively, for specific examples. It will be understood that other devices developed in accordance with the systems and methods described herein may be a different size, a different weight, a different shape, or some combination of a different size, a different weight, or a different shape.

In an example embodiment, the sensor box 112 may be another size, another shape, another weight or some combination of these, as discussed above. The differences may be based on the specific components used to implement the systems and methods described herein and an approach to house those components. In an illustrated example, the GPS module 104 may sit on top of the sensor box 112 and may have a cover, such as a thin plastic cover (e.g., which may be 3D-printed) over the GPS module 104 to protect the GPS module 104 from exposure to the user, exposure to the elements, or both exposure to the user and exposure to the elements. The trade-offs of using this cover are (1) the cover may limit the potential number of satellites in view and (2) the cover may limit the received signal strength compared to when the device is initialized under an open sky with an unobstructed line of sight. However, GPS signals may not be completely blocked off when the cover is on, so the device may be able to find a fix to the GPS satellites.

As illustrated in FIG. 1, various components, e.g., microprocessor 102, memory 106, GPS module 104, or other components 108, 110, may be mounted to a device that may be attached or mounted to the shoe, e.g., within a sensor box. In another example embodiment, one or more of the components may be built into the shoe, rather than in a sensor box. For example, one or more of the microprocessor(s) 102, the GPS 104 (e.g., GPS chip, GPS module, or GPS integrated circuit), memory 106, pressure sensors 108, tubes 110, and so forth may be built into the shoe.

In another example, certain systems and methods described herein may be built into or encapsulated by the shoe. For example, a microprocessor 102, GPS module 104, memory 106, barometric sensors 108, tubes 110, or other components may be incorporated into the shoe. For example, one or more of tubes 110 or a portion of tubes 110 may, instead, be channels in the shoe. In an example embodiment, for privacy reasons, the user has the option to disable the location functionality, such as that provided by the GPS module 104.

FIG. 2 illustrates the bottom surface of a pair of shoe soles 200 of a smart shoe system 100, with labeled sensing points (e.g., sensors 108) at each of the silicone tube coils, in accordance with an exemplary embodiment. For this wearable technology, sampling may occur at a constant high rate when used for gait rehabilitation analysis, which may make the device less efficient from a daily monitoring perspective. When considering a person sitting, there may be relatively little change in a GCF signal. Continuous high sampling may be unnecessary for this situation because the collection of extra data samples may not be useful when the person is not walking, where GCF signals see more changes. Thus, in an example, the sensors may be sampled less often as compared to sampling when a user is determined to be walking. In another example, less data may be taken by only polling one sensor or by only polling one sensor at a time. The single sensor polling may take place at the same frequency as when all sensors 108 are read for gait rehabilitation or at a higher or lower frequency.

In an example embodiment, a feedback controller algorithm is used to dynamically adjust the sampling frequency of the smart shoe's sensors in order to improve the lifetime of an activity recognition system. Each health device has that particular health device's own purpose and features, so a unique adaptive sampling algorithm based on the device's capabilities may be needed or used to improve the system efficiency.

As mentioned before, healthcare professionals typically only see their patients when they visit facilities. Therefore, the full picture about their patients' activities outside these times may not be entirely known. Accordingly, having contextual data may come in useful for daily monitoring. Collected contextual data may provide information about where a patient is spending his or her time for daily activities and may also be used as a means for understanding how a person's environment affects his or her lifestyle and health. A Global Positioning System (GPS) is one such device that may provide contextual data with temporal and spatial information, which may be used for tracking or mapping a user's path. For example, contextual data with temporal and spatial information presented in that time and location may be gathered from a GPS-equipped inhaler at instances when asthmatics needed a dose of medication to investigate what environments may trigger an individual's symptoms. Moreover, to find out what influenced the spread of schistosomiasis, an endemic parasitic disease associated with water contact, researchers may utilize spatiotemporal data to create a map of participants' previous day to help them in an interview where they were to recall past activities and when they contacted water. For daily physical activity and health monitoring, contextual information may let caregivers know when patients were not engaging in physical activities or not following advised instructions such as restricting consumption of fast food.

Systems and methods described herein may include a pair of smart shoes for daily activity and health monitoring of patients involved in outpatient interventions or rehabilitation. An example embodiment may include (1) developing an adaptive sampling algorithm based on identified human activities to optimize or at least improve data size, and/or (2) integrating GPS module 104 with smart shoes to obtain a traveled path of a user that may complement the recorded GCFs to understand the context behind his or her daily activities (e.g., sitting down at a restaurant verses going for a walk at a nearby park).

Figure 3:
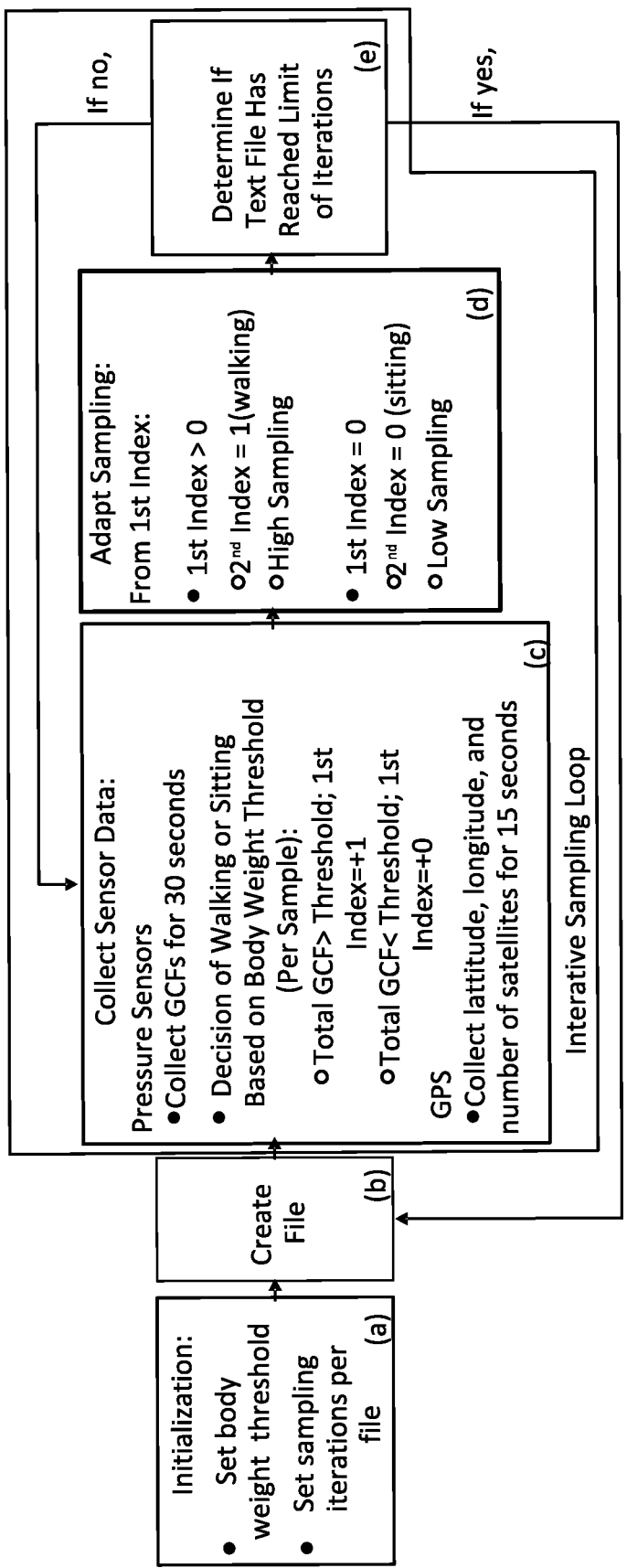
FIG. 3 illustrates a flow chart of an exemplary adaptive sampling algorithm in accordance with various exemplary embodiments.
Figure 4:
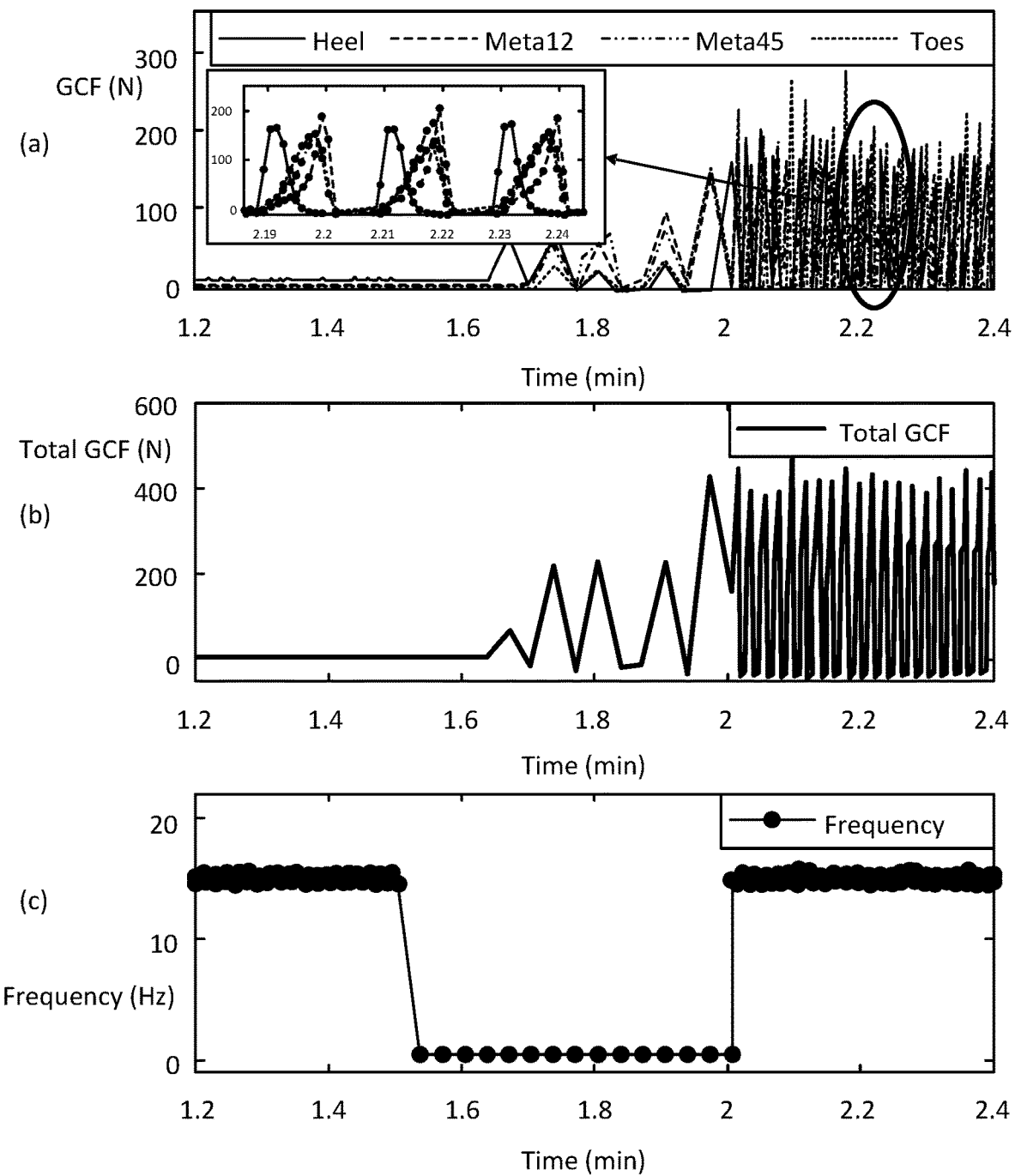
FIG. 4 illustrates exemplary algorithm results for a sitting to walking transition of a user of an exemplary smart shoe system in accordance with an exemplary embodiment.
Figure 5:
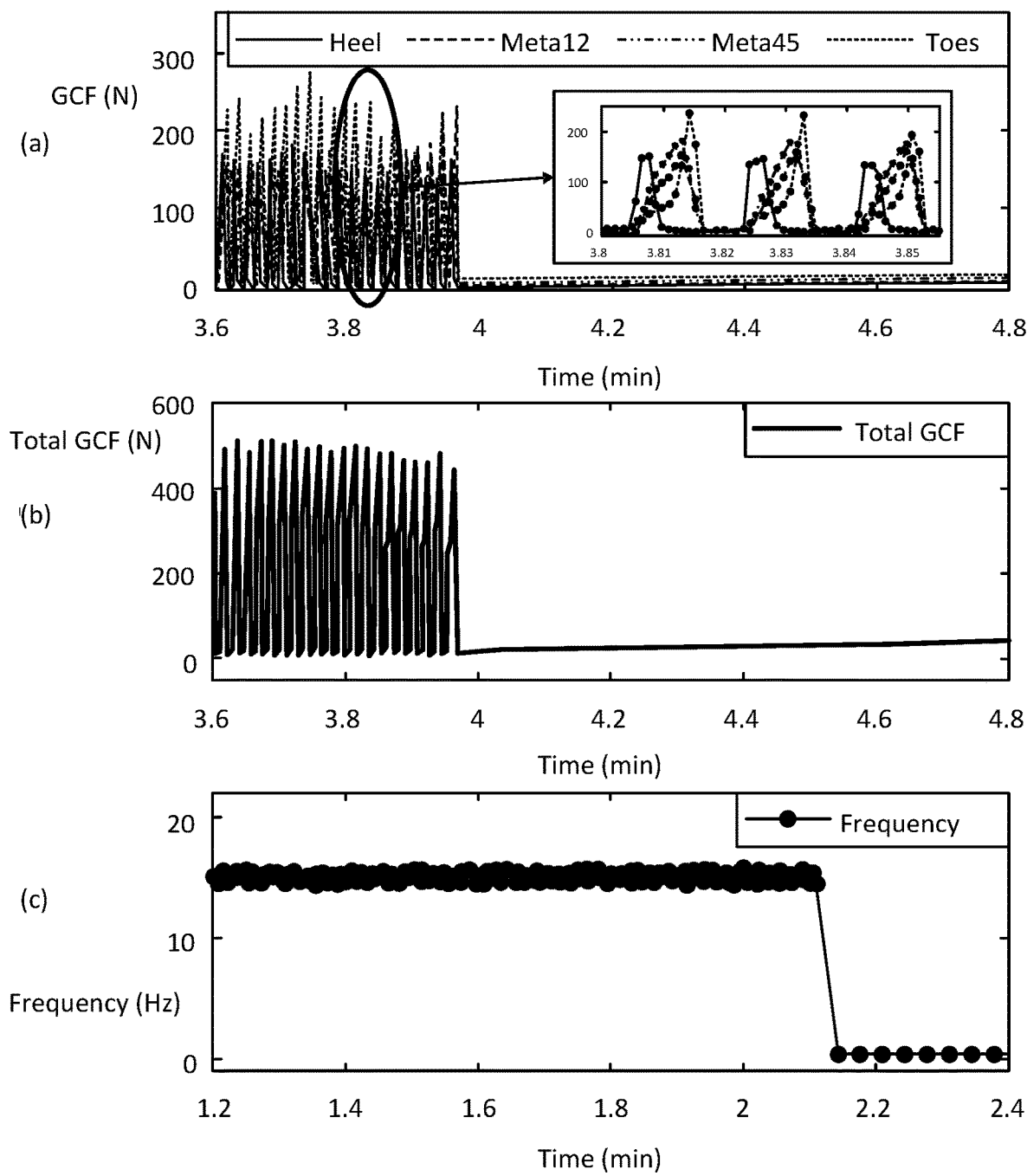
FIG. 5 illustrates exemplary algorithm results for a walking to sitting transition of a user of an exemplary smart shoe system in accordance with an exemplary embodiment.

Turning now to FIGS. 3, 4, and 5, in various exemplary embodiments system 100 utilizes an adaptive algorithm to reduce the amount of data stored, the amount of data transmitted, or both the amount of data stored, and the amount of data transmitted while maintaining an acceptable level of monitoring fidelity. For example, when system 100 determines that a wearer of system 100 is in a sitting position, a data sampling rate may be decreased. Conversely, when system 100 determines that a wearer of system 100 is in a walking position or otherwise engaging in significant movements, a data sampling rate may be increased. In this manner, a data sampling rate appropriate for a given level of movement may be utilized, thus avoiding both unnecessary collection of excess data, as well as insufficient collection of needed data.

FIG. 3 illustrates a flow chart 300 of an exemplary adaptive sampling algorithm in accordance with various exemplary embodiments. FIG. 3 describes an exemplary adaptive sampling algorithm to reduce the size of collected data to contain only useful GCFs. The algorithm tunes the sampling rate of the pressure sensors 108 and the update rate of the GPS module 104 based on different activities, e.g., walking and sitting. (It will be understood, however, that the algorithm may be tailored to other activities, combinations of other activities, or to combinations of other activities including one or more of walking and sitting.) Walking may be considered as being physically active, while sitting may be considered as being stationary. It should also be noted that standing may be grouped into the same category as walking, but this application may generally focus on walking versus sitting for the algorithm's activity detection. Because how people stand and sit is variable, standing may be considered as having a generally even distribution of body weight between both legs, and sitting may be considered as having both feet resting either flat on the floor or completely off the floor.

In accordance with an example embodiment, Table I summarizes the sampling rate of the pressure sensors 108 and update rate of the GPS module 104 when detected as walking (e.g., high sampling) or sitting (e.g., low sampling). For moderate-intensity walking, cadence may be about 100 steps per minute, which translates to about 0.83 Hz stride frequency, or 1.2 seconds per stride. Setting the high sampling rate to 15 Hz allows for a collection of more data points desirable to analyze active movements with better accuracy. Based on the same reasoning about gathering enough data points to accurately capture an activity, the lowest sampling was chosen as 0.5 Hz. Too low of a frequency could result in increased inaccuracy of activity detection for walking, because about one gait cycle may be missed per sample. And, depending on what sample point was taken during a gait cycle, the GCFs that define walking could be missed, causing the inability to detect that activity.

In an example embodiment, other activities may be analyzed to determine a characteristic frequency of movements of that activity. From the characteristic frequency of movements of the activity, a sampling rate for that activity may be selected that may allow sufficient data points to characterize that activity. Accordingly, data for other activities than walking and sitting may be collected by the systems and methods described herein. Moreover, different activities may have overlapping sampling rates. For example, one inactive activity may use the same sampling rate as another inactive activity, e.g., sitting and laying down. Similarly, in some cases, one active activity may use the same sampling rate as another active activity, e.g., walking and slowly jumping. Conversely, one active activity may use a different sampling rate from another active activity when the level of activity is different, e.g., walking and jogging or running. In an example, the systems and methods described herein may "observe" a user at one or more sampling rates over a period to characterize different types of activities the user performs and determine sampling rates for those activities. For example, a device may use the highest sampling rate during this observation period. However, other, lower sampling rates may also be used. Particularly when the systems and methods described herein determine that an activity is inactive or has a lower activity level than another, e.g., by using a higher sampling rate first or by observing that a lower sampling rate returns meaningful data. The user may be asked to name and/or characterize activities during this observation period. For example, a user may characterize an activity like running as being more active than walking.

As discussed above, in an example embodiment, the algorithm may tune the sampling rate of the pressure sensors 108 and the update rate of the GPS module 104 based on the activities of walking and sitting. In another example, the algorithm may tune the sampling rate of the pressure sensors 108 and the update rate of the GPS module 104 based on sensing other activities or a combination of other activities that a user may perform. In an example, the activities may include a combination of walking and sitting, as well as other activities, e.g., running, hopping, crawling, biking, climbing, skipping, dancing, otherwise moving one's feet, or other physical (or not so physical) activities.

For example, generally, the pressure sensors 108 may be able to determine how many steps the patient has taken by determining how many times one or more pressure sensors 108 on a shoe have an increase in pressure followed by a decrease in pressure, e.g., as each foot is placed on the ground and picked up while walking, jogging, running, hopping, skipping, dancing, or otherwise moving one's feet. Furthermore, using GPS module 104, the system may differentiate movement from shuffling from foot to foot or tapping a foot while standing in place. Additionally, velocity may be determined allowing for a prediction of when a user is walking, jogging, or running. Yet further, when increases pressure and decreases in pressure for each shoe approximately coincide with each other, this may indicate hopping. The magnitude of the pressure changes may also provide indications of the level of activity. For example, when a patient is jumping up and down, the higher the patient jumps, the higher the pressure changes may be relative to lower jumps for that patient, assuming the patient is similar in size and weight at each of the times the measurements are taken.

The update rates of the GPS module 104 may, in one example, be based on predefined settings with 1 Hz being the most reliable fast update rate and 0.2 Hz being the lowest update rate that aligns closest to the pressure sensors' 108 low settings. These are example values set for these parameters to illustrate the adaptive sampling concept but may be optimized or modified to increase the algorithm's efficiency. Moreover, any suitable sampling rate may be utilized, as desired.

TABLE 1

Specifications of High Sampling for
Walking and Low Sampling for Sitting

| Sampling Settings | Sampling of Pressure Sensors | Update of GPS |
|---|---|---|
| High | 15 Hz | 1 Hz |
| Low | 0.5 Hz | 0.2 Hz |

In an example embodiment, a threshold of 47.5% of the user's body weight may be defined to classify the activities, but body weight may be a tuning parameter set by medical professionals or machine learning algorithms for specific patients. As mentioned previously, the algorithm may be utilized to detect standing as a physical activity. With the assumption that full body weight is distributed evenly or approximately evenly across both right and left feet when standing normally, meaning each side should measure 50% or approximately 50% body weight in GCFs, the threshold for one shoe may need to be below the 50% value to make the detection. Body weight percentage may be arbitrarily set to 95% of 50% (47.5% of body weight) with intentions to account for potential variations in GCF signals that fall below the assumed 50% value when standing but do not make the body weight low enough to trigger high sampling when sitting. The threshold may be calculated prior to beginning the adaptive sampling algorithm by collecting GCFs from all four pressure sensors 108 for, e.g., 15 seconds, as the user stands still on one leg (assumed as applying full body weight, because assumption of half body weight when standing normally might be inaccurate due to uneven weight distribution between the right and left legs), summing all GCFs in each sample set for a total GCF estimate, averaging the sums, and proportioning the averaged value to 47.5%. From the flow chart of the algorithm in FIG. 3, 30 seconds was chosen as the window of time to collect pressure sensor 108 data prior to deciding a user state such as walking or sitting. In other example embodiments, other periods may be used, such as periods between 1 second and 60 seconds, or more. The example of a 30 second period allows time for maintaining high sampling when walking with brief pauses of standing and beginning reduction of sampling for more prolonged periods of sitting. The GPS module 104 and pressure sensors 108 may be set to run on independent pathways to collect data simultaneously. However, for the GPS module 104 to change the GPS module 104's update rate, the GPS module 104 may use information regarding what activity has been detected by the pressure sensors 108. There may be a chance that the GPS module 104 pathway just misses the newly detected activity change from the pressure sensors 108 when the GPS module 104 pathway is also set to collect data evenly 30 seconds, resulting in a false detection duration of 30 seconds. For this reason, the GPS module 104 may be set to check the activity detected by the pressure sensors 108 at a predetermined rate, e.g., every 15 seconds, which is an arbitrary value with safety margin meant to reduce the time that the GPS module 104 update rate takes to match the activity detected by the pressure sensors 108 when the GPS module 104 does in fact make a false detection. The smaller the value this is, the better the algorithm may perform since the potential duration of time that the GPS module 104 and the pressure sensors 108 do not match in rates may be minimized.

Following the diagram in FIG. 3, an example algorithm may be sequenced as (a) initialization, (b) creating a new file, (c) collecting sensor data, (d) adapting sampling, and (e) determining if a test has reached a limit on iterations.

For initialization, a user may set a body weight threshold by standing on the leg of interest (e.g., the side with a mounted sensor box 112 on the shoe) for a period, e.g., a predetermined period, for example, 15 seconds. Other periods, e.g., from 1 to 30 seconds or longer may be used. For initialization, a user may also set the number of sampling iterations per file, where one iteration may be equal to one 30-second interval. Other periods, e.g., from 1 to 60 seconds or longer may be used. Generally, after initialization, a new text file may be created.

For collecting sensor data, e.g., at sampling intervals, GCFs may be collected from the pressure sensors 108 over a predetermined duration, e.g., 30 seconds. Other periods, e.g., from 1 to 30 seconds or longer may be used, however. During this time, all four GCFs from each sensing point may be combined per sample for a total GCF. This total GCF may be compared to the body weight threshold. When the total GCF is above the threshold, a first index number (initially starting at zero and resetting every 30-seconds or some other interval) may be incremented by 1. A value below the threshold may increment the first index by 0. This first index may be an accumulating number whose final value at the end of the 30-second interval may determine what activity the user is engaged in. In an example embodiment, GPS data may be collected over a predetermined period, e.g., 15 seconds to minimize the duration of false detection. Other periods, e.g., from 1 to 30 seconds or longer may be used, however.

With adaptive sampling, in an example, after each 30-second interval (or other periods, e.g., from 1 to 30 seconds or longer may be used, however) from the pressure sensors 108, a second index number may be updated to reference the most recent detected activity. The second index may be set to either 1 for walking or 0 for sitting based on the last updated value of the first index before the first index resets for the next interval.

After each 15-second interval from the, e.g., GPS module 104, the update rate may be set to the lowest sampling when the second index given by the pressure sensors 108 is equal to 0 (sitting) and may be set to the highest sampling when the second index is equal to 1 (walking). Other periods, e.g., from 1 to 30 seconds or longer may be used for the GPS module, however.

In an example, once the maximum iterations per file has been reached, a new file may be created and the sampling iterations resume. When the maximum iterations per file have not been reached, then the algorithm may continue the iterative sampling loop including collecting sensor data and adapting the sampling.

The examples above include various example periods, e.g., 15 seconds, 30 seconds, 60 seconds, etc. It will be understood that other periods may be used, e.g., from >0 seconds to 60 seconds or more. Furthermore, index numbers of 0 and 1 are used in the illustrated example. It will be understood, however, that other index values, including numbers greater than 1 or even negative numbers may be used for the index numbers. The times and numbers may be selected based on the level of activity and/or the measurement being taken.

In an example, a test was performed to validate the adaptive sampling algorithm. A healthy female human subject who is 53.2 kg and 1.5 m tall was asked to conduct an outdoor scenario of the device's use with the sensor box 112 mounted onto the right smart shoe. Based on preliminary testing, the algorithm showed to perform best when the device was under minimal changes in surrounding temperature and away from excessive heat. Given the nature of the pneumatic system, significant temperature variations between different environments may cause GCFs to offset from initialized values resulting in inaccurate activity detections from the algorithm; therefore, automatic and/or manual re-calibration and/or re-zeroing may be utilized, as appropriate. Also, exposure to high temperatures for too long may damage electrical components and melt the plastic housing. Therefore, an outdoor test conducted on a cooler summer day may be used to assess the performance of the algorithm. For post-processing purposes, "zero" GCF values for each pressure sensor 108 were initialized at the beginning of a test to adjust any offsets within the incoming force measurements. However, in an example, this step may be omitted from the algorithm. Measurements of interest were GCFs, latitude, and longitude of the subject and recorded frequency from pressure sensors 108.

For this test, the subject: allowed some time for the device to adjust to environment temperature when bringing the device from indoors to outdoors; started the device; initialized the "zero" GCF values for each sensing point by lifting the right foot with the smart shoe off the ground for 15 seconds; stood on right foot for 15 seconds to allow the algorithm to determine the threshold; sat down for 1 minute; walked for 2 minutes; sat down for 1 minute.

The times for each activity were not exact because of the structure in the outdoor environment but were followed closely. An aside experiment compared the result of continuously running the adaptive sampling algorithm to continuously running the device at two extremes the maximum potential of the system (baseline) and the lowest sampling for the algorithm.

For a baseline test the pressure sensors 108 were sampling on average 226 samples per second and the GPS module 104 was updating at 1 Hz, e.g., the maximum working settings for all sensors. Test 1 was a test of the smart shoes with algorithm. Test 2 was a test of the pressure sensors 108 sampling on average at about 0.5 Hz, with the GPS module 104 updating at 0.2 Hz.

For each test, a smart shoe was powered on by a fully charged 400 mAh 3.7 V LiPo battery and left alone until the battery was completely drained. Battery efficiency was assumed to be constant between each test. Conditions at the extremes were tested three times each for an average run-time per condition, while running the smart shoes with the algorithm was tested once. The reason for this was that the test involved the spontaneous actions of the subject wearing the shoes, meaning that an exact test could not be replicated.

For the final experiment, the same subject from the main test was to wear the shoes for a duration of a fully-charged battery to record latitude and longitude from her daily activities, which demonstrated the use of contextual data when monitoring an individual's day.

FIG. 4 illustrates exemplary algorithm results for a sitting to walking transition of a user of the exemplary smart shoe system 100 in accordance with an exemplary embodiment. Similarly, FIG. 5 illustrates exemplary algorithm results for a walking to sitting transition of a user of the exemplary smart shoe system 100 in accordance with an exemplary embodiment. FIGS. 4 and 5 are the results of the recorded GCFs from all four pressure sensors 108 (FIGS. 4*a* and 5*a*), the total GCF estimates (FIGS. 4*b* and 5*b*), and the recorded sampling rate from the pressure sensors 108 (FIGS. 4*c* and 4*c*). In FIGS. 4*a* and 5*a*, an expanded time-base (zoom-in) of a portion of the segments when walking (e.g., the segments that are circled on the main figures) are incorporated onto the original GCF plots to better illustrate what the four GCF signals for walking look like when recorded at 15 Hz.

Specifically, in FIG. 4, recorded GCFs, total GCF estimates, and a sampling rate of the pressure sensors 108 during the transition from sitting to walking are illustrated. Transitioning from sitting to standing was observed some time just after 1.6 minutes based on the total GCF estimates as seen in FIG. 4*b*, changing from a relatively constant value to fluctuating gait patterns. The sampling rate did not increase until after 2 minutes, because the algorithm was still collecting GCFs to identify that the subject was walking between a 10-second interval. Once the sampling was increased, GCF patterns when walking began to look more normal than the initial steps taken during low sampling. Within this window of time, 645 samples were recorded.

FIG. 5 illustrates the GCFs from each of the sensors, the total GCF estimates, and the recorded sampling rate of the pressure sensors 108 when the subject transitioned from walking back to sitting. It was observed that the sampling rate remained high for some time after the subject sat back down at about 4 minutes (comparing FIGS. 5*b* and 5*c*), because the sampling rate was not reduced until the total GCFs remained lower than the threshold for one 30-second interval. FIG. 5*b* illustrates sampling reduction at roughly 4.5 minutes where the subject had sat down for at least 30 seconds. There were 836 samples recorded in this time frame.

For the duration of this test, which was about 5 minutes, the sampling algorithm recorded 3,212 samples. For roughly the same amount of time from the highest settings from both sensors (not the highest sampling of the algorithm), 67,679 samples were recorded, which means the algorithm reduced collected samples by 95% while still including all useful gait information of that period.

In Table 2 below are the average operable run-times, in minutes, for each of the sampling rate conditions. Upon post-processing, operable run-times were estimated at the time that the first barometric sensor began to have a significant drop in magnitude of readings meaning that the current battery level could no longer sustain powering the device. For baseline testing at the device's maximum sampling potential, the average run-time was 169 minutes. Reducing to the lowest settings increased the average run-time by 37.3% to 232 minutes. The algorithm may have an increase in run-time somewhere in the middle at about 225 minutes, which was a 33.1% increase from the baseline. Because the adaptive sampling algorithm allows for a higher sampling rate only when necessary during detected physical activity, the adaptive sampling algorithm reduces how much battery operation time may be sacrificed. The operating time using the algorithm may be as close as the operating time with just low sampling (depending on what activities are detected from the user) as seen in the results from Table 2 between Test 1 and Test 2.

TABLE 2

Operable Run-Times

|  | Operable | % Increase from Baseline | Standard Deviation |
|---|---|---|---|
| Baseline | 169 (Average) | N/A | 0.90 |
| Test 1 | 225 | 33.1% | N/A |
| Test 2 | 232 (Average) | 37.3% | 4.62 |

Figure 6:
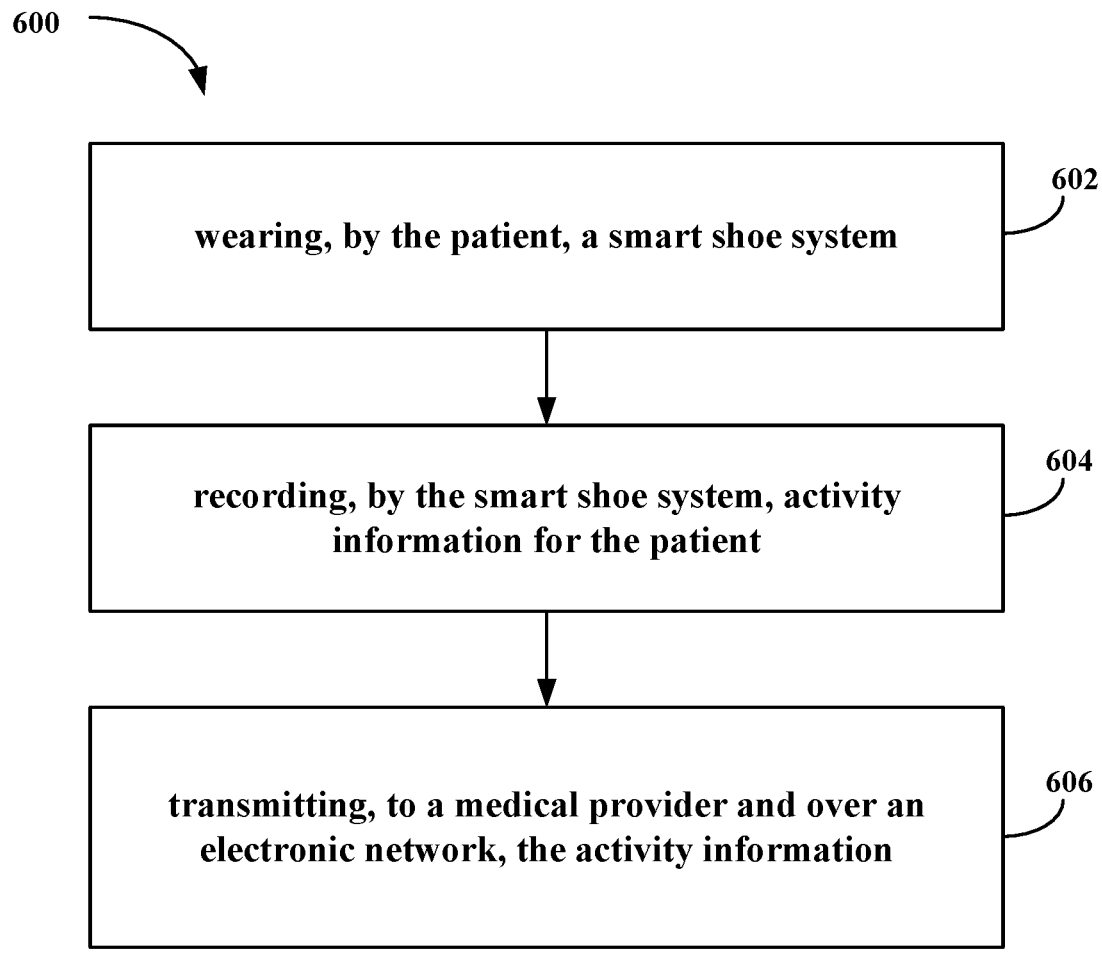
FIG. 6 illustrates a flow chart of an exemplary method in accordance with various exemplary embodiments.

FIG. 6 illustrates a flow chart 600 of an exemplary method in accordance with various exemplary embodiments. The exemplary method may be a method for monitoring an activity level of a patient. The method may include wearing, by the patient, a smart shoe system 100 (step 602). Additionally, the method may also include recording, by the smart shoe system 100, activity information for the patient (step 604). The method may also include transmitting, to a medical provider and over an electronic network, the activity information (step 606). Based at least in part on the activity information, the medical provider may take an action, such as communicating with the patient (e.g., by telephone, email, text message, mobile application, electronic assistant, and/or the like), communicating with a medical facility, scheduling an appointment with the patient, modifying a treatment plan for the patient, beginning a treatment plan for the patient, ceasing a treatment plan for the patient, contacting emergency services, and/or the like.

As discussed above, the method may include wearing, by the patient, a smart shoe system 100 (step 602). For example, the patient may wear the smart shoe while exercising or throughout the day during normal daily activities. Wearing the smart shoe while exercising may allow a user to track activity information while exercising. Wearing the smart shoe throughout the day during normal daily activities may allow a user to track activities for the whole day, or at least the portion when the patient is wearing the shoe, e.g., assuming the smart shoe is operating correctly during the entire period.

Additionally, the method may also include recording, by the smart shoe system 100, activity information for the patient (step 604). Activity information may include, but is not limited to, activity data generated by a plurality of pressure sensors 108. The activity data may allow for determinations of activity such as sitting and walking. For example, the algorithm may tune the sampling rate of the pressure sensors 108 and the update rate of the GPS module 104 based on different activities, e.g., walking and sitting. Walking may be considered as being physically active, while sitting may be considered as being stationary, physically inactive, or not physically active.

The method may also include transmitting, to a medical provider, e.g., over an electronic network, the activity information (step 606). Accordingly, in an example embodiment, the smart shoe system 100 may include a radio frequency transceiver for wireless communication between the smart shoe method and other electronic networking components.

In an example embodiment, the shoe may have a plurality of pneumatic pressure sensors 108. The pressure sensors 108 may be configured to detect pressure at a plurality of points in the sole 200 of the shoe. A microprocessor 102 may be coupled to the pressure sensors 108 and a GPS integrated circuit (e.g., part of the GPS module 104) for correlating position of the smart shoe system 100 to activity data generated by the plurality of pressure sensors 108.

In an example embodiment, the system may include a memory 106, e.g., flash memory storage for storing data generated by the microprocessor 102 and pressure sensors 108.

In an example embodiment, the microprocessor 102 of the smart shoe system 100 may execute an adaptive algorithm to select a data sampling rate for the plurality of pressure sensors 108. The adaptive algorithm may be the algorithm of FIG. 3.

In an example embodiment, the sampling rate may be selected from the range between 0.5 Hertz and 15 Hertz. However, other sampling rates may be selected, including higher and lower sampling rates.

In an example embodiment, the smart shoe system 100 used may further include a battery coupled to the microprocessor 102, the GPS integrated circuit (e.g., part of the GPS module 104), and the pressure sensors 108.

While the principles of this disclosure have been shown in various embodiments, many modifications of structure, arrangements, proportions, the elements, materials and components, used in practice, which are particularly adapted for a specific environment and operating requirements may be used without departing from the principles and scope of this disclosure. These and other changes or modifications are intended to be included within the scope of the present disclosure.

The present disclosure has been described with reference to various embodiments. However, one of ordinary skill in the art appreciates that various modifications and changes can be made without departing from the scope of the present disclosure. Accordingly, the specification is to be regarded in an illustrative rather than a restrictive sense, and all such modifications are intended to be included within the scope of the present disclosure. Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, required, or essential feature or element.

As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. Also, as used herein, the terms "coupled," "coupling," or any other variation thereof, are intended to cover a physical connection, an electrical connection, a magnetic connection, an optical connection, a communicative connection, a functional connection, and/or any other connection. When language similar to "at least one of A, B, or C" or "at least one of A, B, and C" is used in the specification or claims, the phrase is intended to mean any of the following: (1) at least one of A; (2) at least one of B; (3) at least one of C; (4) at least one of A and at least one of B; (5) at least one of B and at least one of C; (6) at least one of A and at least one of C; or (7) at least one of A, at least one of B, and at least one of C.

What is claimed is:

1. A smart shoe system for monitoring patient activity, the smart shoe system comprising:
   a shoe having a plurality of pressure sensors, each pressure sensor in the plurality of pressure sensors configured to detect pressure at a plurality of points in a sole of the shoe;
   a microprocessor coupled to the plurality of pressure sensors;
   a Global Positioning System ("GPS") integrated circuit for correlating position of the smart shoe system to activity data generated by the plurality of pressure sensors; and
   a flash memory storage for storing data generated by the microprocessor and the plurality of pressure sensors, the microprocessor configured to execute an adaptive algorithm comprising:
   initializing the adaptive algorithm;
   creating a new file;
   determining, based on a pressure data received from the plurality of pressure sensors, a transition from a sitting phase to a walking phase;
   adapting a sampling rate for the plurality of pressure sensors, the adapting including augmenting a first sample rate for the plurality of pressure sensors to a second sample rate for the plurality of pressure sensors for the walking phase;
   augmenting a first update rate for the GPS integrated circuit to a second update rate for the GPS integrated circuit for the walking phase;
   collecting sensor data including storing the pressure data and a location data recorded during the sitting phase and the walking phase in the flash memory storage; and
   determining if a test has reached a limit on iterations.

2. The smart shoe system of claim 1, wherein the first sample rate and the second sample rate are within a range between 0.5 Hertz and 15 Hertz, the first sample rate being less than the second sample rate.

3. The smart shoe system of claim 1, further comprising a battery coupled to the microprocessor, the GPS integrated circuit, and the plurality of pressure sensors.

4. The smart shoe system of claim 3, further comprising a radio frequency transceiver for wireless communication between the smart shoe system and other electronic networking components, the microprocessor further configured to transmit, through the radio frequency transceiver, the pressure data and the location data.

5. A method for monitoring an activity level of a patient, the method comprising:
   wearing, by the patient, a smart shoe system;
   executing an adaptive algorithm to select a data sampling rate for a plurality of pressure sensors, the adaptive algorithm comprising (a) initialization, (b) creating a new file, (c) collecting sensor data, (d) adapting sampling from a first sample rate to a second sample rate, and (e) determining if a test has reached a limit on iterations;
   recording, by the smart shoe system, activity information for the patient, the activity information including pressure data and location data, wherein:
   the pressure data is recorded at the first sample rate during a sitting phase in response to the smart shoe system determining the patient is sitting,
   the pressure data is recorded at the second sample rate during a walking phase in response to the smart shoe system determining the patient is walking,
   the location data is recorded at a first update rate during the sitting phase in response to the smart shoe system determining the patient is sitting, and
   the location data is recorded at a second update rate during the walking phase in response to the smart shoe system determining the patient is walking;
   storing the pressure data and the location data recorded during the sitting phase and the walking phase in the smart shoe system; and
   transmitting, to a medical provider and over an electronic network, the activity information.

6. The method of claim 5, wherein the first sample rate and the second sample rate are within a range between 0.5 Hertz and 15 Hertz, the first sample rate being less than the second sample rate.

7. The method of claim 5, wherein the transmitting the activity information includes transmitting, via a radio frequency transceiver, the activity information wirelessly between the smart shoe system and other electronic networking components.

8. The method of claim 5, wherein the smart shoe system comprises:
   a shoe having the plurality of pressure sensors, the plurality of pressure sensors configured to detect pressure at a plurality of points in a sole of the shoe;
   a microprocessor coupled to the plurality of pressure sensors;
   a Global Positioning System ("GPS") integrated circuit for correlating position of the smart shoe system to activity data generated by the plurality of pressure sensors; and
   a flash memory storage for storing data generated by the microprocessor and the plurality of pressure sensors.

9. The method of claim 8, wherein the smart shoe system further comprises a battery coupled to the microprocessor, the GPS integrated circuit, and the plurality of pressure sensors.

10. A smart shoe having a sole, the smart shoe comprising:
    a plurality of pressure sensors, each pressure sensor in the plurality of pressure sensors configured to detect pressure at a plurality of points in the sole of the smart shoe;
    a microprocessor coupled to the plurality of pressure sensors;
    a Global Positioning System ("GPS") integrated circuit for correlating position of the smart shoe to activity data generated by the plurality of pressure sensors; and
    a flash memory storage for storing data generated by the microprocessor and the plurality of pressure sensors, the microprocessor configured to execute an adaptive algorithm comprising:
    initializing the adaptive algorithm;

creating a new file;

determining, based on pressure data received from the plurality of pressure sensors, a transition from a sitting phase to a walking phase;

adapting a sampling rate for the plurality of pressure sensors, the adapting including augmenting a first sample rate for the plurality of pressure sensors to a second sample rate for the plurality of pressure sensors for the walking phase;

augmenting a first update rate for the GPS integrated circuit to a second update rate for the GPS integrated circuit for the walking phase;

collecting sensor data including storing the pressure data and a location data recorded during the sitting phase and the walking phase in the flash memory storage; and determining if a test has reached a limit on iterations.

11. The smart shoe of claim 10, wherein the first sample rate and the second sample rate are within a range between 0.5 Hertz and 15 Hertz, the first sample rate being less than the second sample rate.

12. The smart shoe of claim 10, further comprising a battery coupled to the microprocessor, the GPS integrated circuit, and the plurality of pressure sensors.

13. The smart shoe of claim 10, further comprising a radio frequency transceiver for wireless communication between the smart shoe and other electronic networking components.

* * * * *